United States Patent [19]

Lawrence et al.

[11] Patent Number: 4,935,041
[45] Date of Patent: Jun. 19, 1990

[54] PHOTOLYSIS APPARATUS AND COLLECTION TRAP MODULE

[75] Inventors: Lowell J. Lawrence; Abbe L. Kesterson; Steven B. Jackson, all of Lexington, Ky.; Luis O. Ruzo, Berkley, Calif.; Terry L. Johnson, Lexington, Ky.

[73] Assignee: Pharmacology & Toxicology Research Lab., Lexington, Ky.

[21] Appl. No.: 416,845

[22] Filed: Oct. 4, 1989

Related U.S. Application Data

[62] Division of Ser. No. 255,112, Oct. 7, 1988.

[51] Int. Cl.⁵ .......................... G01N 1/22; B01D 53/00
[52] U.S. Cl. .......................................... 55/244; 55/256; 261/22; 261/122; 422/102; 422/88; 137/384; 73/863.21
[58] Field of Search ........... 73/863.21, 863.83, 864.34, 73/865.6, 864.73, 864.74, 864, 864.51; 422/88, 101, 102; 261/119.1, 121.1, 22, 122; 55/244, 255, 256; 137/384

[56] References Cited

U.S. PATENT DOCUMENTS

| Re. H229 | 3/1917 | Phillips | 73/865.6 |
| 996,991 | 7/1911 | Little | 55/256 |
| 4,018,908 | 4/1977 | Gross | 426/281 |
| 4,051,626 | 10/1977 | Trumley et al. | 47/17 |
| 4,129,427 | 12/1978 | Harris | 55/256 X |
| 4,224,828 | 9/1980 | Steinke | 73/863.21 |
| 4,291,674 | 9/1981 | Cumte et al. | 126/419 |
| 4,791,820 | 12/1988 | Lawrence et al. | 73/863.21 |
| 4,827,778 | 5/1989 | Bossert et al. | 73/863.21 |

Primary Examiner—Tom Noland

[57] ABSTRACT

An apparatus for the collection of volatiles includes a housing that forms an environmental chamber. Dishes of test sample are placed in this chamber which is closed with a transparent cover. A gasket assures an airtight seal between the cover and the housing. The housing is supported on a stand that allows the angular orientation of the housing to be adjusted relative to the path of the sun. A jacket is also formed in the housing about the environment chamber. A heat exchange fluid is circulated through this jacket to maintain the environmental chamber and, thus, the test sample within a desired temperature range. Volatiles emitted by the test sample are collected by circulating air through the environmental chamber. This air which passes across the test sample dishes serves to sweep up the volatiles which are then delivered to a collection trap for qualitative and quantitative analysis. The collection trap is formed from one or more modules including a vessel or tube that is closed by a vapor collection adapter. An O-ring seal between the tube and vapor collection adapter ensures an airtight seal. The vapor collection adapter is also provided with cooperating ball and socket connectors on an outlet and inlet respectively that allow for connection of two or more modules in series as desired.

5 Claims, 3 Drawing Sheets

PHOTOLYSIS APPARATUS AND COLLECTION TRAP MODULE

This is a division of application Ser. No. 255,112 filed Oct. 7, 1988.

TECHNICAL FIELD

The present invention relates generally to the chemical apparatus field and, more particularly, to a test apparatus specially designed for use in collecting volatiles from a test sample undergoing soil photolysis study. The invention also relates to a unique collection trap especially adapted for this and other like purposes.

BACKGROUND OF THE INVENTION

Over the years the agricultural and forestry industries have turned increasingly to science to help feed and house the ever increasing human population. Through the development of various herbicides, fertilizers, insecticides and pesticides for terrestial crop and forest uses, man has been able to markedly improve the productivity of the land. The increases in crop and timber production, however, have not been obtained without suffering some adverse consequences.

More particularly, many of the herbicides, fertilizers, insecticides and pesticides that have been developed detrimentally impact the environment in one way or another when used in certain concentrations or under certain conditions. Livestock poisonings, fish kills and other cataclysmic events have resulted. For example, many insecticides such as DDT are particularly stable and resistant to destruction by light and oxidation. With continued use, concentrations of such insecticides may build up in the environment over time to dangerous levels. This may lead to widespread death of wild life and contamination of water supplies deleteriously affecting downstream population centers.

The problem has not gone unnoticed by the government. The Environmental Protection Agency has recently devised new tests specifically designed to collect the data necessary for evaluating the hazard inherent in these types of chemical compounds. One of the studies developed by the government for evaluating the overall environmental impact of, for example, a pesticide is a full degradation study of the pesticide on the surface of a soil sample.

Pesticides may be intentionally applied to the soil surface, remain on the soil surface due to incomplete soil incorporation or reach the soil surface via drift and/or run off from treated areas. Pesticides on the soil surface may undergo photolytic transformation by sunlight. Photolysis is the interaction of a compound with light. More specifically, light energy is transferred to the chemical bonds of the compound, either directly or indirectly through another compound. This energy serves to break the bonds and the original compound is transformed to another compound or compounds known as photoproducts. The purpose of the soil photolysis studies is to provide data on pesticide degradation rates and on the formation and decline of photoproducts on soil surfaces. It is important to complete soil studies since a photoproduct formed on soil may react with the soil organic matter or be metabolized by soil microorganisms, thus producing possibly unique degradation products. In order to determine potential hazards of the pesticide the rates of photolysis and half lives of the parent pesticide and its photodegradates must be studied and determined in order to establish the importance of the transformation process and the persistence characteristics of photoproducts that may be formed.

Exacting test procedures have been developed to accurately determine the rates of soil surface photolysis of pesticides and to identify photoproducts and rates of formation and decline of these products. Procedures are standardized so that results of various studies, even when conducted by different groups, may be effectively compared.

Preferably, the test samples are exposed to natural sunlight conditions. Thus, the environmental chamber for containing the test samples must be supported in a way so as not to block the passage of light to the samples. In addition, the environmental chamber must include an optically pure wall allowing the passage of natural sunlight to the test samples without filtering any of the radiation.

Of course, the passage of light into the environmental chamber tends to heat the chamber. In fact, the soil surface holding the test samples within the environmental chamber could reach temperatures nearly twice that experienced in the actual environment where the particular pesticide would be sprayed. These higher temperatures could cause reactions and the production of unique photoproducts that would not occur in the lower soil temperatures of the actual environment. Because of this, the apparatus should also include a temperature control mechanism for maintaining the temperature of the test samples and soil within a desired range approaching that of the actual environment in which the pesticide is to be used.

A further concern relates to the need to minimize the loss of test sample through volatilization. In order to accurately determine the photolysis rate of the test sample, the volatiles emitted by the test sample should be collected. Further, these volatile photoproducts should be identified if emitted in any appreciable level. Thus, in order to carry out this procedure, the environmental chamber must be sealed and provide some means for collecting the emitted volatiles. In addition, it is preferred that at least a portion of the test sample and soil be available for convenient recovery from the environmental chamber to allow periodic testing at specific time intervals. This will allow the identification of degradation products that may, be produced by the reaction of photoproducts with the soil organic matter or the metabolization of those products by soil microorganisms.

To date, the present inventors are unaware of any apparatus that has been developed that may be used to effectively meet the criteria discussed above. A need, therefore, exists for a simple and effective apparatus that may be utilized in performing soil photolysis studies.

SUMMARY OF THE INVENTION

Accordingly, it is a primary object of the present invention to provide an apparatus of relatively simple construction that may be conveniently used to collect volatiles from a test sample.

Another object of the present invention is to provide an apparatus for the collection of volatiles from a test sample undergoing degradation studies that may be oriented to expose the test samples to the full radiation of the sun while allowing for full control of the environmental temperature during testing.

Still another object of the present invention is to provide a collection trap module that may be linked together with other such modules in series for the multiway trapping of volatiles.

Still another object of the present invention is the provision of a collection trap module providing a sealed system of highest integrity for consistent flow while also eliminating contamination problems commonly associated with rubber stopper sealed test tube trap designs.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved apparatus is provided for the collection of volatiles from a test sample. More specifically, the apparatus is especially adapted for the collection of volatiles produced during soil photolysis studies of a test sample, such as presently required under Environmental Protection Agency regulations.

The apparatus of the present invention includes a housing that forms an environmental chamber. A series of dishes including, for example, soil and test sample may be positioned in the environmental chamber. A transparent cover closes the environmental chamber. Preferably, the transparent cover is formed from quartz so that the full range of radiation produced by the sun is allowed to pass through and reach the test sample in the dishes. In order to ensure that the entire test sample is exposed to the light of the sun, the housing includes an adjustable stand. More particularly, the stand allows the orientation of the housing to be adjusted so that the transparent cover and underlying sample containing Petri dishes are held in a plane substantially perpendicular to the path of the sun.

In order to ensure an airtight seal, a gasket composed of, for example, ethylene propylene is provided between the transparent quartz cover and the housing. Clamps are also provided to ensure that the transparent cover is fixed to the housing with the gasket disposed therebetween providing an airtight seal.

The environmental chamber also includes an inlet passage in one end and an outlet passage at an opposing end that allow the circulation of gas across the chamber. In addition, a jacket is provided surrounding the walls of the environmental chamber on five sides. A heat exchange fluid, such as ethylene glycol, is circulated through the jacket. In the jacket the ethylene glycol is held in heat transfer relationship with the walls of the environmental chamber so as to allow the control of the temperature in the chamber throughout the study.

More specifically, the apparatus is provided with a pump for circulating gas through the inlet and across the environmental chamber over the dishes to the outlet. From the outlet, volatiles swept up in the gas are conveyed to a collection trap.

Preferably, the collection trap is modular in form. Each collection trap module includes a vessel for holding a collection solvent. The type of solvent utilized may be determined by the type of voltatiles that are expected to be produced. The collection trap module also includes a vapor collection adapter that engages and closes the vessel. This vapor collection adapter serves to direct the incoming gas and volatiles from the environmental chamber into the vessel and through the collection solvent. A gasket is provided for sealing and connecting the vapor collection adapter with the vessel. This gasket is designed to seat within a groove formed about the mouth of the vessel and in the cooperating end of the vapor collection adapter. By clamping the vapor collection adapter and vessel together with the gasket disposed in the seating groove, a tight, substantially leakproof seal is provided.

Advantageously, the improved integrity of this seal assures that consistent flow is provided through the trap. This serves to increase the trapping efficiency of the apparatus.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

Figure 1:
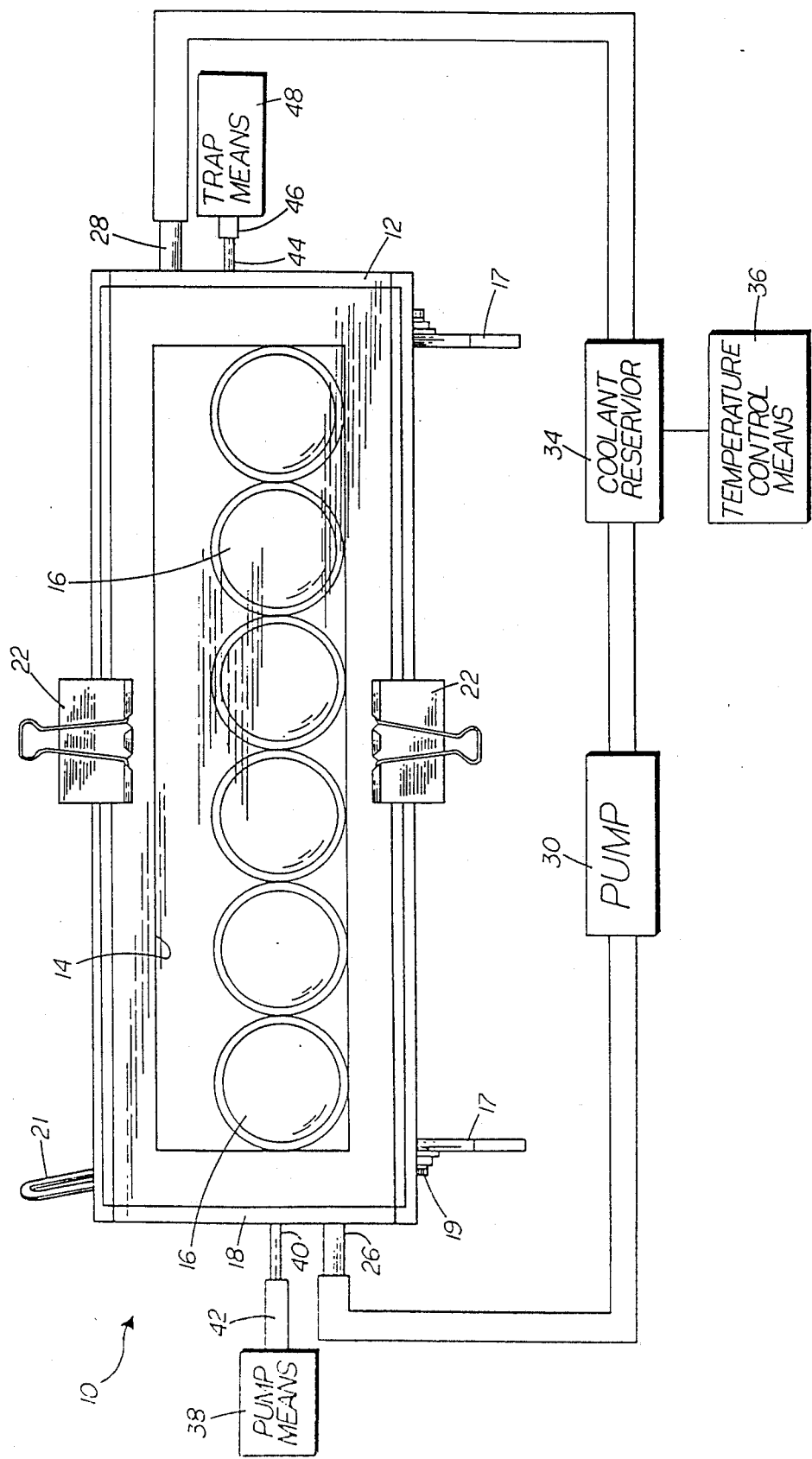
FIG. 1 is a top plan partially schematic view of the volatile collection apparatus of the present invention.
Figure 2:
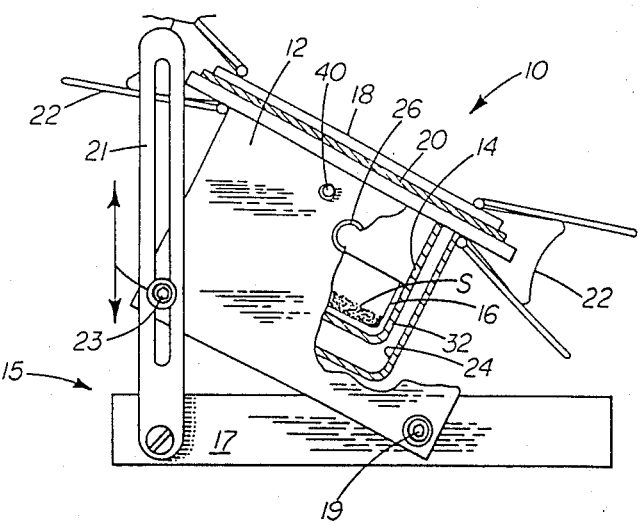
FIG. 2 is a partially broken away end elevational view of the apparatus of the present invention showing a temperature control jacket surrounding the environmental chamber.

Reference is now made to FIGS. 1 and 2 showing the apparatus 10 of the present invention for utilization in the collection of volatiles emitted from a test sample S. The invention is being described with respect to the collection of volatiles from a test sample undergoing soil photolysis studies. It should be appreciated, however, that the invention in its broader aspects is not limited to such a specific application, but is being shown in this manner only for purposes of illustration.

As shown in FIGS. 1 and 2, the apparatus includes a housing 12 constructed of, for example, stainless steel. Formed in the housing is an environmental chamber 14.

The chamber 14 is especially adapted to hold a series of containers such as Petri dishes 16. As shown, each dish 16 includes a layer of soil and test sample S. For example, soil from the area in which a pesticide is to be utilized is passed through a 2 mm sieve, then air dried and sterilized. Approximately 3.1 gm of the soil is then added to each 50 mm dish 16. This soil is then made into a slurry by the addition of 3 ml of sterile distilled water. The slurry is then allowed to air dry, thereby forming a layer on the bottom of each dish 16 having a thickness of approximately 0.5 mm.

The soil surface area of each dish 16 is approximately 19.6 cm$^2$ or $4.8 \times 10^{-7}$ acres. An amount of pesticide test sample S equivalent to that applied to this size area when used properly in the environment is then applied to the soil in each dish 16. The dishes 16 are then placed in the environmental chamber 14.

The housing 12 rests on a stand 15 that allows the angular orientation of the housing to be adjusted so that the dishes 16 are held on a plane substantially perpendicular to the sun. This ensures that the radiation of the sun directly impinges on the entire surface of the soil and test sample S held in each dish 16.

As shown in FIG. 2, the stand 15 includes a base leg 17 at each end of the housing that rests on the ground. A pin 19 pivotally connects the housing 12 to the one leg 17 along the lower front margin of the housing. An elongated guide track 21 is pivotally mounted to the rear of that base leg 17. A locking bolt 23 extends through the slot in the guide track 21 and engages the lower rear margin of the housing 12. The locking bolt 23 is loosened to move the rear of the housing 12 up and down along the guide track 21 until the desired angular orientation of the housing is reached. The bolt 23 is then tightened to lock the housing 12 in position.

A transparent cover 18 closes the top of the environmental chamber 14. Preferably, the transparent cover 18 is constructed of optically pure material such as quartz which does not tend to absorb and transmit different wave lengths to any appreciable extent. Thus, the full spectrum of the sun's radiation passes through the cover 18 to the test sample S held in the dishes 16.

A substantially airtight seal is provided between the cover 18 and the housing 12. More particularly, as best shown in FIG. 2, a gasket or seal 20 of relatively inert material such as ethylene propylene is disposed between the transparent cover 18 and the upper face of the housing 12. Clamps in the form of spring clips 22 may be utilized to clamp the cover 18 to the housing 12 with the gasket 20 disposed therebetween. While only two clips 22 are shown in FIGS. 1 and 2, preferably, clips are provided about the entire periphery of the housing 12 and cover 18 even at the ends to ensure a substantially airtight seal.

As shown in FIG. 2, a jacket 24 is formed in the housing 12 about the environmental chamber 14. An inlet 26 and outlet 28 communicate with the jacket 24. Where it is desired to maintain a substantially constant temperature during soil photolysis studies, a heat exchange fluid such as ethylene glycol may be circulated through the jacket 24. Thus, as shown in FIG. 1, a pump 30 may be provided to pump ethylene glycol through the inlet 26 into the jacket 24. There the ethylene glycol is held in heat transfer relationship with the walls 32 of the environmental chamber 14. This serves to maintain the temperature in the environmental chamber 14 at a substantially constant level such as at 25° C.$\pm$5°. After the ethylene glycol circulates through the jacket 24 in contact with the walls 32, it exits through the outlet 28 and returns to a reservoir 34. A temperature control apparatus 36 such as are known in the art may be positioned in heat exchange relationship with the reservoir 34 to allow the temperature of the ethylene glycol to be adjusted to any desired level.

During testing, volatiles emitted by the test sample S held in the enviromental chamber 14 are collected by the circulation of air. More particularly, a pump 38 is connected to the environmental chamber inlet 40 by means of a line 42. Gas from the pump 38 passes through the inlet 40 into the environmental chamber 14. The air then moves across the open dishes 16 so as to sweep volatiles emitted by the test sample S in each dish toward the environmental chamber outlet 44. The gas and volatiles then flow from the outlet 44 through the line 46 to a collection trap 48 shown schematically in FIG. 1. There the gas and volatiles are bubbled through, for example, sulfuric acid, sodium hydroxide solution and/or ethylene glycol depending on the types of volatiles that may be expected to be produced. The trap 48 serves to collect volatiles for quantitative and/or qualitative analysis as desired, with the gas medium either being recycled by the pump 44 or exhausted to the atmosphere.

Figure 3:
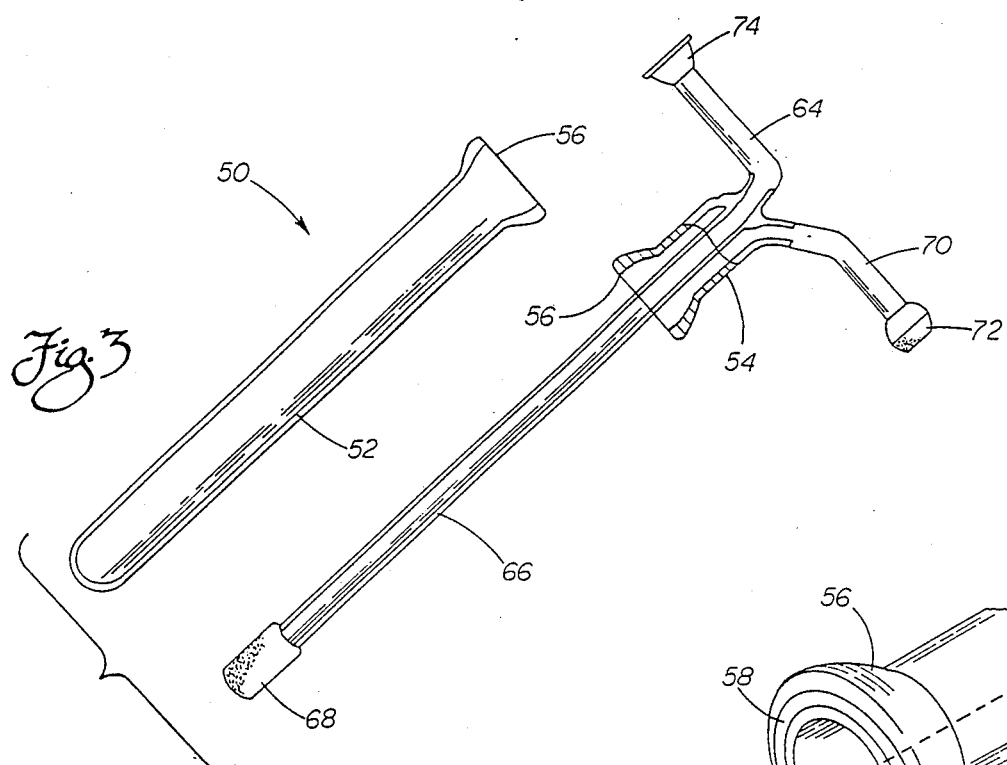
FIG. 3 is an exploded, partly cross-sectional view of the vessel and vapor passage adapter of a collection trap module of the present invention.
Figure 5:
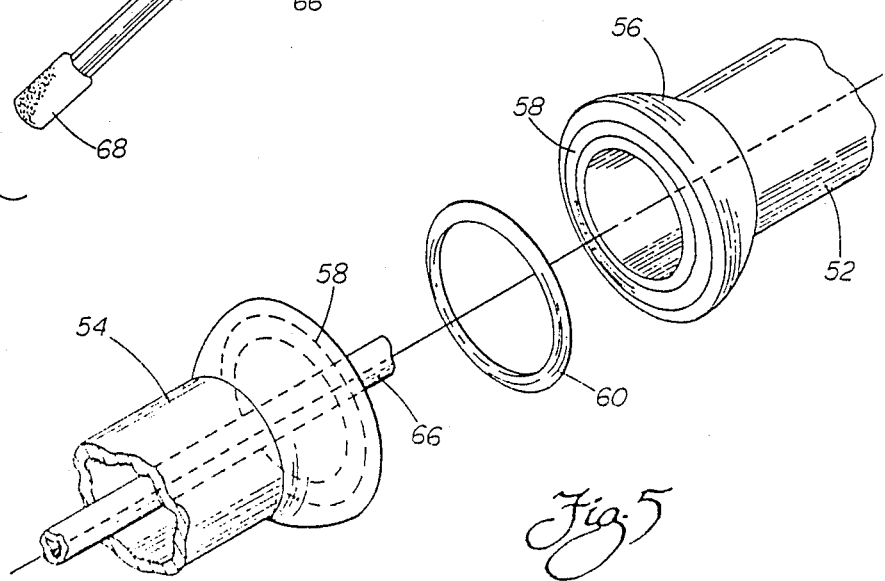
FIG. 5 is a detailed end perspective view showing the O-ring gasket and grooved end of the vapor collection adapter in which the O-ring seats.

More specifically, the collection trap 48 may be formed by one or more collection trap modules 50 (see FIG. 3). Each collection trap module 50 includes a vessel in the form of an elongated tube 52. A selected collection solvent C is placed in the tube 52. The top of the tube 52 is then sealed by means of a vapor collection adapter 54. Both the tube 52 and adapter 54 include enlarged ends 56 especially adapted to be joined together. Each end includes an annular groove 58. An O-ring gasket 60 seats in the grooves 58. Thus, when the tube 52 and adapter 54 are clamped together with a spring clamp 62, a fully airtight seal is provided.

Preferably, the O-ring gasket 60 is made from a highly inert fluorocarbon material such as available from E. I. Dupont de Nemours under the trademark VITON. Advantageously, such a material is unlikely to react with the solvents or volatiles and, therefore, the potential for contamination of the collected products is significantly reduced.

The vapor collection adapter 54 includes an inlet 64 designed specifically to direct a gas stream, such as air, downwardly through a tube 66 to a glass frit 68 adjacent the closed, bottom end of the tube 52. The frit 68 serves to disperse the gas in the collection solvent. The dispersed gas bubbles upwardly through the solvent C and that portion of the gas not dissolved in the solvent passes through the outlet 70 of the vapor collection adapter 54. The gas may then be directed from the outlet 70 through another module 50, recycled by the pump 38 through the environmental chamber 14 or vented to the atmosphere as desired.

Figure 4:
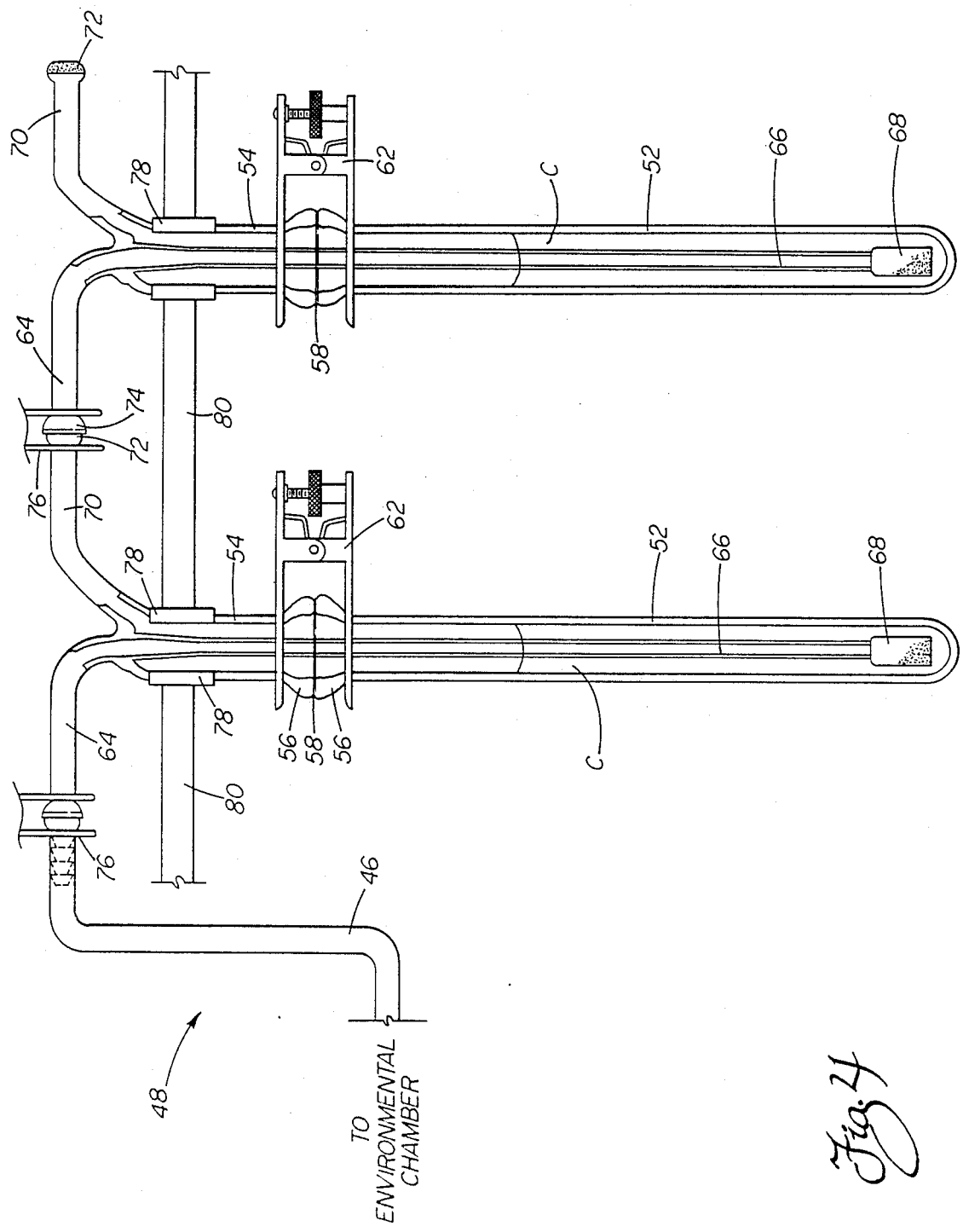
FIG. 4 shows two of the collection trap modules of the present invention connected together in series.

In conducting certain studies of test samples such as soil photolysis studies for the Environmental Protection Agency, it may be desirable for a number of the modules 50 to be connected in series or building block fashion. The manner in which this is done is best shown in FIG. 4. As should be appreciated also from viewing FIG. 3, each vapor collection adapter 54 includes cooperating ball and socket connectors 72, 74 especially adapted for this purpose. More specifically, a ball 72 is mounted to the distal end of each outlet 70. A cooperating socket 74 is mounted to the distal end of each inlet 64. The ball and socket connectors 72, 74 are shaped to cooperate and provide for full sealing engagement. A spring clamp 76 may be utilized to maintain the connectors 72, 74 together and provide the necessary seal to prevent the loss of volatiles from the ball and socket joint of adjacent modules 50.

A collection trap 48 of the type described provides a number of distinct advantages. More particularly, the tight seals provided by the ball and socket connector 72, 74 and O-ring gaskets 60 prevent leakage so as to provide even, consistent flow of vapors through the collection trap 48 at all times whether it includes single or multiple modules 50. By substantially eliminating the possibility of sudden changes in the flow rate due to the development of leaks, the possibility of collection solvent bubbling up into the area of the O-ring seal (i.e. between the tube 52 and adapter 54), or through an outlet 70 into an adjacent module 50 is substantially avoided. As such, excellent trapping efficiency is achieved.

During certain procedures such as degradation studies, it may also become necessary to analyze the collected volatiles at periodic intervals. This may be done conveniently and efficiently with the collection trap 48 described above. Initially, the pump 38 is deactivated to stop all gas flow. The clamp 62 holding the particular tube 52 including the volatiles to be tested is then loosened and removed. The tube 52 including the collection solvent C is then removed for further testing while the associated vapor collection adapter 54 is held fixed in position by means of the clamp 78 which is attached to the test stand 80. A new tube 52 with or without collection solvent S is then reattached to the vapor collection adapter 54 with the clamp 62. Then the pump 38 is restarted. In this way, the remaining modules 50 of the collection trap 48 remain undisturbed and the loss of volatiles is absolutely minimized. This simple procedure advantageously serves to eliminate a number of potential errors that could be made during testing that might significantly affect test results.

In summary, numerous benefits have been described which result from employing the concepts of the present invention. The orientation of the apparatus 10 of the present invention may be adjusted so as to ensure that the light from the sun is cast across the entire surface of the soil and test sample held in the dishes 16. If desired, a dish including test sample may be removed from the environmental chamber 14 at periodic intervals to confirm the presence of starting materials and photoproducts on the surface of the soil at any particular time after application. Advantageously, the remaining sample dishes 16 remain undisturbed. The temperature of the environmental chamber 14 may also be maintained within a relatively narrow range substantially corresponding to that expected to be found in the environment in which the pesticide being tested is going to be utilized.

A unique collection trap 48 is also provided. Advantageously, the O-ring connection between the vapor collection adapter 54 and the tube 52 of each module 50 substantially eliminates contamination and prevents any possiblity of leaks. As such, a relatively constant rate of flow of vapors through the collection trap is maintained. Thus, spillovers of solvent from one module 50 to another are avoided. In addition, volatiles collected in a particular module 50 may be periodically checked without disturbing other modules in the collection trap series.

The foregoing description of the preferred embodiment of the invention has been presented for purposes of illustration and description. It is not intended to be exhaustive or to limit the invention to the precise form disclosed. Obvious modifications or variations are possible in light of the above teachings. The preferred embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A collection trap module for collecting volatiles, comprising:
    vessel means including a mouth and closed end for holding a collection solvent;
    a vapor collection adapter for engaging and closing said mouth of said vessel means, said vapor collection adapter serving to direct vapor into said vessel means and through said collection solvent;
    gasket means for sealingly connecting said vapor collection adapter with said vessel means; and
    a seating groove formed in an end of said vessel means about said mouth and in a cooperating end of said vapor collection adapter, said gasket means being received in said seating groove to tightly seal said vessel means and vapor collection adapter together.

2. The collection trap set forth in claim 1, wherein said vapor collection adapter includes an inlet tube for directing volatiles down into said collection solvent adjacent said closed end of said vessel means.

3. The collection trap set forth in claim 1, wherein said vapor collection adapter includes an outlet tube for directing volatiles passing through said collection solvent from said vessel means.

4. The collection trap set forth in claim 1, further including means for serially connecting one collection trap module in series with another collection trap module.

5. The collection trap set forth in claim 4, wherein said vapor collection adapter includes inlet and outlet tubes and said connecting means includes cooperating ball and socket connectors mounted to distal ends of said inlet and outlet tubes.

* * * * *